United States Patent
Kato et al.

(10) Patent No.: US 6,529,764 B1
(45) Date of Patent: Mar. 4, 2003

(54) PUNCTURE NEEDLE SUPPORT TOOL, RF COIL, MAGNETIC RESONANCE SIGNAL MEASURING APPARATUS, AND MAGNETIC RESONANCE IMAGING APPARATUS AND METHOD

(75) Inventors: Yasushi Kato, Tokyo (JP); Masaaki Sakuma, Tokyo (JP); Kenji Suzuki, Tokyo (JP)

(73) Assignee: Ge Yokogawa Medical Systems, Limited, Tokyo (JP)

( * ) Notice: Subject to any disclaimer, the term of this patent is extended or adjusted under 35 U.S.C. 154(b) by 180 days.

(21) Appl. No.: 09/644,334

(22) Filed: Aug. 23, 2000

(30) Foreign Application Priority Data

Oct. 5, 1999 (JP) .......................................... 11-284168

(51) Int. Cl.[7] ................................................ A61B 5/05
(52) U.S. Cl. ....................................... 600/411; 324/318
(58) Field of Search ................................. 600/411, 422, 600/562, 417, 407, 415; 324/318, 309, 319, 321

(56) References Cited

U.S. PATENT DOCUMENTS

| | | | |
|---|---|---|---|
| 4,465,069 A | 8/1984 | Barbier | |
| 4,727,327 A | 2/1988 | Toyoshima | |
| 5,066,915 A | 11/1991 | Omori | |
| 5,409,497 A | 4/1995 | Siczek | |
| 5,534,778 A | * 7/1996 | Loos et al. | 324/318 |
| 5,585,724 A | * 12/1996 | Morich et al. | 324/318 |
| 5,706,812 A | * 1/1998 | Strenk et al. | 600/417 |
| 5,782,764 A | 7/1998 | Werne | |
| 5,823,960 A | 10/1998 | Marconi | |
| 6,060,883 A | * 5/2000 | Knuttel | 324/318 |

FOREIGN PATENT DOCUMENTS

| | | |
|---|---|---|
| DE | 19808220 | 2/1999 |
| EP | 0757255 | 5/1997 |

* cited by examiner

Primary Examiner—Teresa Walberg
Assistant Examiner—Quang Van
(74) Attorney, Agent, or Firm—Moonray Kojima

(57) ABSTRACT

In order to facilitate appropriate biopsy puncture in magnetic resonance imaging, a puncture needle support tool has a base member 610 attached to an RF coil 200, a slider 630 attached to the base member movably in parallel to the axis of the RF coil, and a puncture needle guide 636 having a puncture needle through hole 638 and an MR marker 640 disposed in parallel to the through hole, capable of linearly moving in a direction perpendicular to the sliding direction on the slider and of rotatively moving in a plane perpendicular to the axis of the RF coil.

8 Claims, 13 Drawing Sheets

FIG. 4
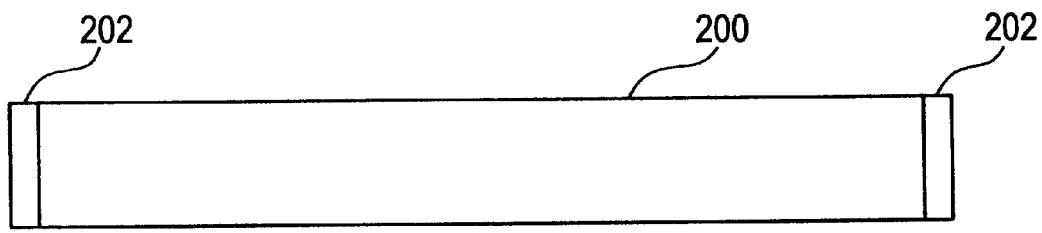
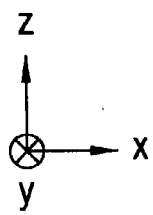
FIG. 5
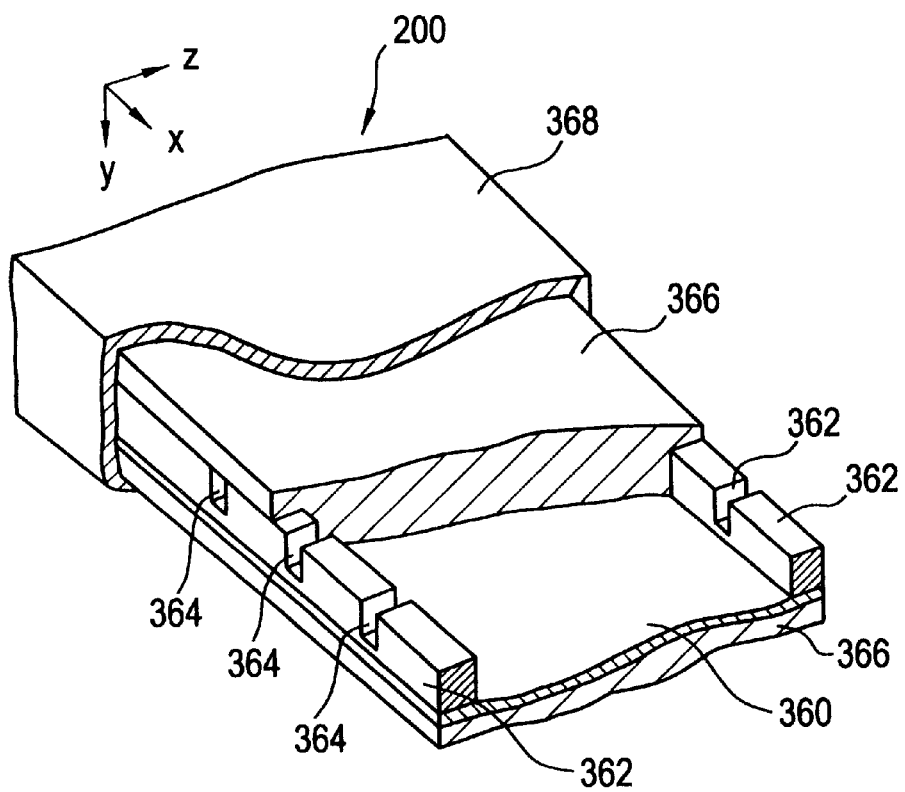

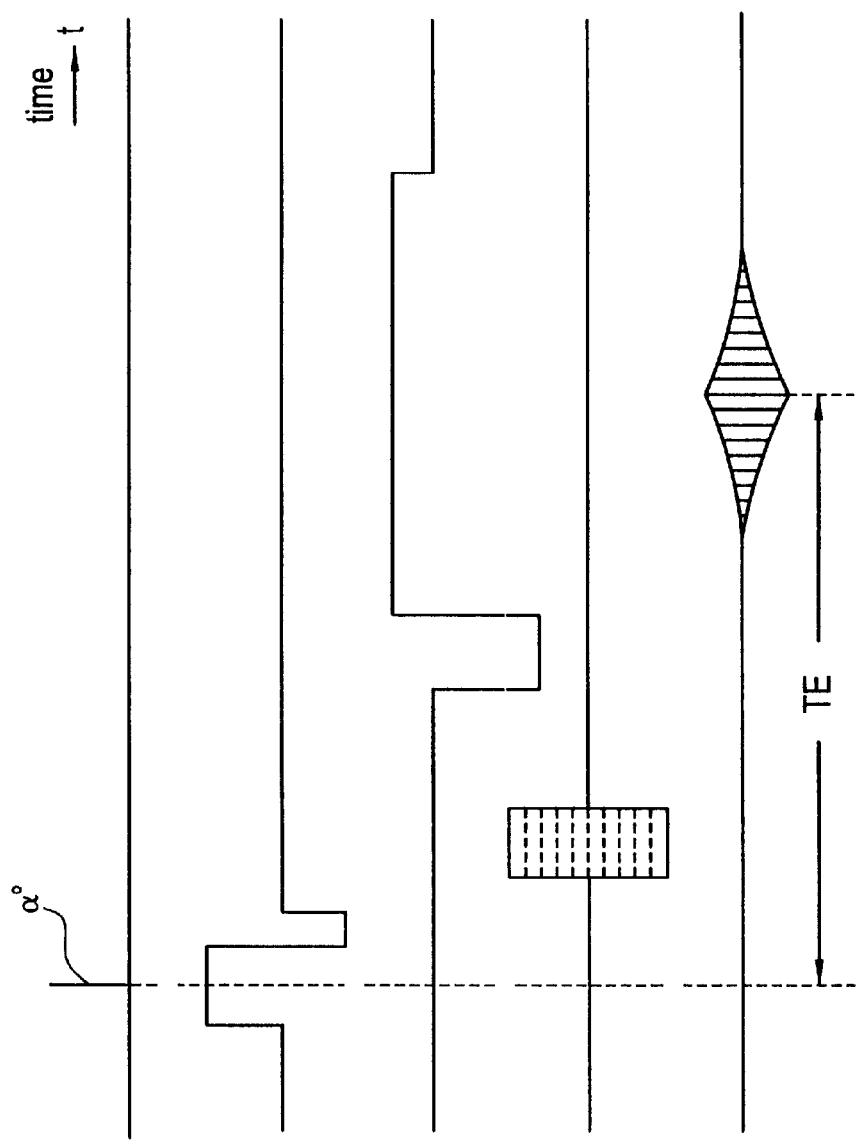
FIG. 17A RF
FIG. 17B Gs
FIG. 17C Gr
FIG. 17D Gp
FIG. 17E MR

PUNCTURE NEEDLE SUPPORT TOOL, RF COIL, MAGNETIC RESONANCE SIGNAL MEASURING APPARATUS, AND MAGNETIC RESONANCE IMAGING APPARATUS AND METHOD

BACKGROUND OF THE INVENTION

The present invention relates to a puncture needle support tool, RF (radio frequency) coil, magnetic resonance signal measuring apparatus, and magnetic resonance imaging apparatus and method, and more particularly to a puncture needle support tool attached to an RF coil, an RF coil provided with the puncture needle support tool, a magnetic resonance signal measuring apparatus employing such an RF coil, and a magnetic resonance imaging apparatus and method employing such a magnetic resonance signal measuring apparatus.

A magnetic resonance imaging apparatus employing a magnetic field generating apparatus with high openness of an imaging space, such as a permanent magnet magnetic field generating apparatus, is employed to perform "interventional" imaging, i.e. magnetic resonance imaging concurrent with a medical operation such as biopsy on an object to be imaged.

In performing biopsy, an RF coil for receiving a magnetic resonance signal is positioned with respect to the object to be imaged so that an object site can be properly imaged, and a puncture needle support tool is positioned with respect to the object to be imaged so that the object site can be properly punctured.

In such a magnetic resonance imaging apparatus, the separate RF coil and puncture needle support tool must be individually positioned. The operative work is therefore complicated. Moreover, since the operator must determine the puncture direction for the puncture needle based on an image being captured, considerable skill is required for the operator to carry out appropriate puncture.

SUMMARY OF THE INVENTION

It is therefore an object of the present invention to provide a puncture needle support tool for facilitating appropriate puncture in magnetic resonance imaging, an RF coil provided with such a puncture needle support tool, a magnetic resonance signal measuring apparatus employing such an RF coil, and a magnetic resonance imaging apparatus and method employing such a magnetic resonance signal measuring apparatus.

In accordance with a first aspect of the invention, there is provided a puncture needle support tool comprising: a first base member having means for attachment to an RF coil; a second base member attached to the first base member movably in a direction substantially parallel to the axis of the RF coil; and a guide member comprising a puncture needle passage and an MR marker disposed along the puncture needle passage, and attached to the second base member movably in a direction substantially perpendicular to the axis of the RF coil and rotatably in a plane substantially perpendicular to the axis of the RF coil.

In accordance with a second aspect of the invention, there is provided an RF coil comprising: a coil body forming a loop adapted to surround an object to be imaged; and a puncture needle support tool engaged with the coil body.

In accordance with a third aspect of the invention, there is provided a magnetic resonance signal measuring apparatus comprising an RF coil and magnetic resonance signal measuring means connected to a body of the RF coil, wherein the RF coil as described regarding the second aspect is employed as the RF coil.

(Effect)

According to the present invention, a puncture needle support tool is integrally engaged with a coil body to improve coordination of positioning of the RF coil and positioning of the puncture needle. Moreover, a guide member for the puncture needle is provided with an MR marker to make it possible to determine the puncture direction based on an image of the MR marker.

Thus, the present invention can provide a puncture needle support tool for facilitating appropriate puncture in magnetic resonance imaging, an RF coil provided with such a puncture needle support tool, a magnetic resonance signal measuring apparatus employing such an RF coil, and a magnetic resonance imaging apparatus and method employing such a magnetic resonance signal measuring apparatus.

Further objects and advantages of the present invention will be apparent from the following description of the preferred embodiments of the invention as illustrated in the accompanying drawings.

BRIEF DESCRIPTION OF THE DRAWINGS

FIG. 4 is an exploded view of a coil body of the receive coil section shown in FIG. 2.

FIG. 5 is a schematic view illustrating the internal structure of the coil body of the receive coil section shown in FIG. 2.

FIGS. 16(A)–16(E) and 17(A)–(E) are schematic diagrams illustrating exemplary pulse sequences executed by the apparatus shown in FIG. 1.

DETAILED DESCRIPTION OF THE INVENTION

Figure 1:
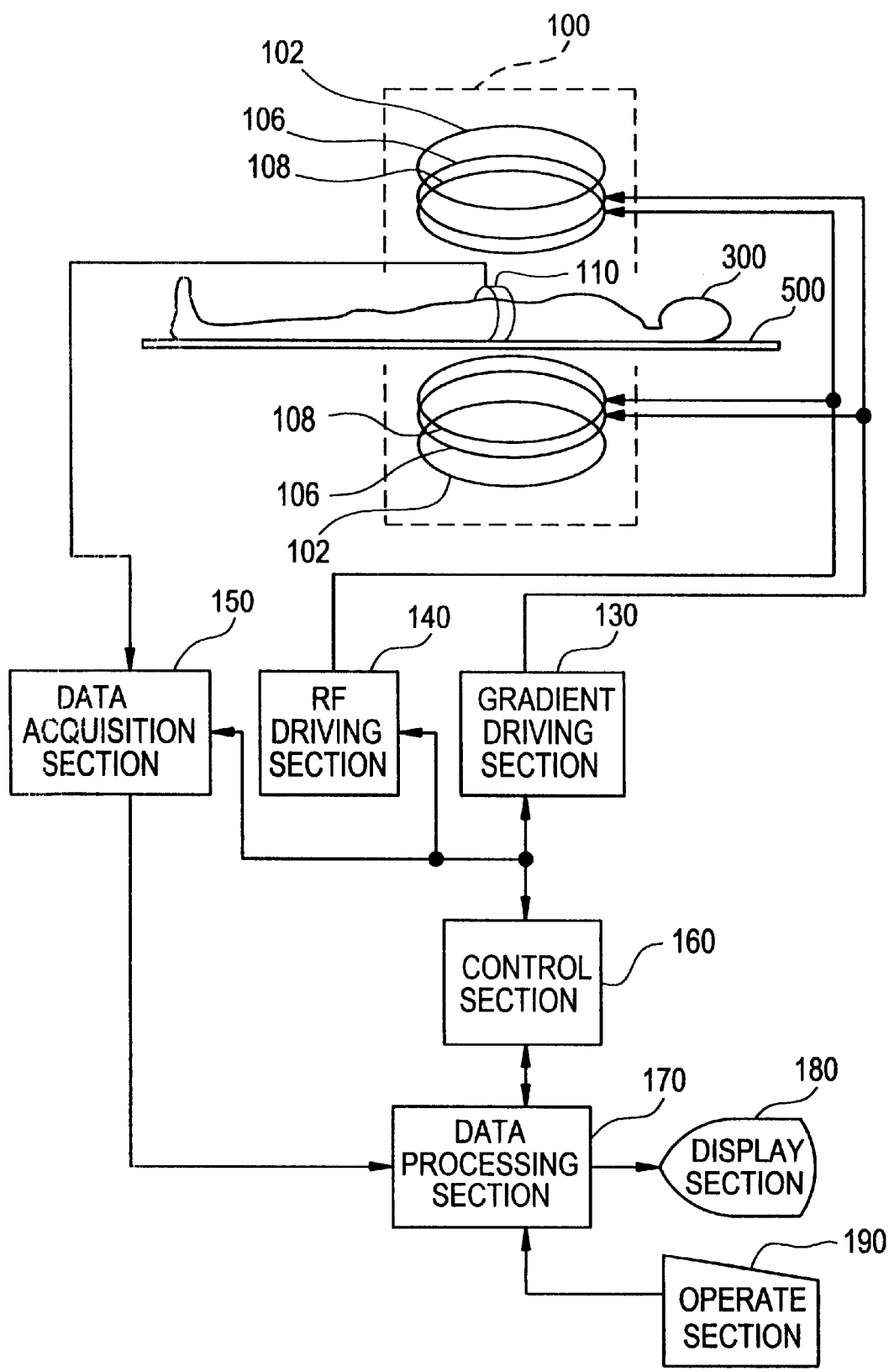
FIG. 1 is a block diagram of an apparatus in accordance with an embodiment of the present invention.

Several embodiments of the present invention will now be described in detail With reference to the accompanying drawings. FIG. 1 shows a block diagram of a magnetic resonance imaging apparatus, which is an embodiment of the present invention. The configuration of the apparatus represents an embodiment of the apparatus in accordance with the present invention, and the operation of the apparatus represents an embodiment of the method in accordance with the present invention.

As shown in FIG. 1, the present apparatus has a magnet system 100. The magnet system 100 has a main magnetic field magnet section 102, a gradient coil section 106 and an RF coil section 108. The main magnetic field magnet section 102 and the coil sections 106 and 108 each comprises a pair of members facing each other across a space. These sections have a generally disk-like outer shape and are disposed to have a common center axis. An object to be imaged 300 is rested on a cradle 500 and carried into and out of the internal space of the magnet system 100 by carrier means (not shown).

The cradle 500 is provided with a receive coil section 110. The receive coil section 110 is attached with a puncture needle support tool, which will be described later. The receive coil section 110 has a generally cylindrical shape and is disposed on the upper surface of the cradle 500. The object to be imaged 300 is placed in a supine position within the cylindrical receive coil section 110.

The receive coil section 110 is an embodiment of the RF coil of the present invention. The configuration of the coil represents an embodiment of the apparatus of the present invention. The receive coil section 110 will be described in more detail later.

The main magnetic field magnet section 102 generates a static magnetic field in the internal space of the magnet system 100. The main magnetic field magnet section 102 is an embodiment of the static magnetic field generating means of the present invention. The direction of the static magnetic field is generally orthogonal to the direction of the body axis of the object to be imaged 300, i.e., a "vertical" magnetic field is generated. The main magnetic field magnet section 102 is made using a permanent magnet, for example. It will be easily recognized that the main magnetic field magnet section 102 is not limited to a permanent magnet, but may be made using a super or normal conductive electromagnet or the like.

The gradient coil section 106 generates gradient magnetic fields for imparting gradients to the static magnet field strength. The gradient magnetic fields to be generated are the following three: a slice gradient magnetic field, a readout gradient magnetic field and a phase encoding gradient magnetic field. The gradient coil section 106 has three gradient coils (not shown) corresponding to these three gradient magnetic fields.

The RF coil section 108 transmits an RF excitation signal to the static magnetic field for exciting spins within the object to be imaged 300. The receive coil section 110 receives a magnetic resonance signal generated by the excited spins.

The gradient coil section 106 is connected with a gradient driving section 130 for supplying driving signals to the gradient coil section 106 to generate the gradient magnetic fields. A portion consisting of the gradient coil section 106 and gradient driving section 130 is an embodiment of the gradient magnetic field generating means of the present invention. The gradient driving section 130 has three driving circuits (not shown) corresponding to the three gradient coils in the gradient coil section 106.

The RF coil section 108 is connected with an RF driving section 140. The RF driving section 140 supplies a driving signal to the RF coil section 108 to transmit the RF excitation signal, thereby exciting the spins within the object to be imaged 300. A portion consisting of the RF coil section 108 and RF driving section 140 is an embodiment of the high frequency magnetic field generating means of the present invention.

The receive coil section 110 is connected with a data acquisition section 150 for gathering signals received by the receive coil section 110 and acquiring the signals as digital data.

A portion consisting of the receive coil section 110 and data acquisition section 150 is an embodiment of the magnetic resonance signal measuring apparatus of the present invention. The configuration of the measuring apparatus represents an embodiment of the apparatus of the present invention. The portion consisting of the receive coil section 110 and data acquisition section 150 is also an embodiment of the measuring means of the present invention. The data acquisition section 150 is an embodiment of the magnetic resonance signal measuring means of the present invention.

The gradient driving section 130, RF driving section 140 and data acquisition section 150 are connected with a control section 160 for controlling these sections 130–150.

The output of the data acquisition section 150 is connected to a data processing section 170. The data processing section 170 stores data gathered from the data acquisition section 150 in a memory (not shown). Thus, a data space is formed in the memory, which constitutes a two-dimensional Fourier space. The data processing section 170 performs a two-dimensional inverse Fourier transformation on the data in the two-dimensional Fourier space to reconstruct an image of the object to be imaged 300. The data processing section 170 is an embodiment of the image producing means of the present invention.

The data processing section 170 is connected to the control section 160. The data processing section 170 is above the control section 160 and controls the section 160. The data processing section 170 is connected with a display section 180 that displays the reconstructed image and several kinds of information output from the data processing section 170, and an operating section 190 that is operated by a human operator and inputs several commands, information and so forth to the data processing section 170.

Figure 2:
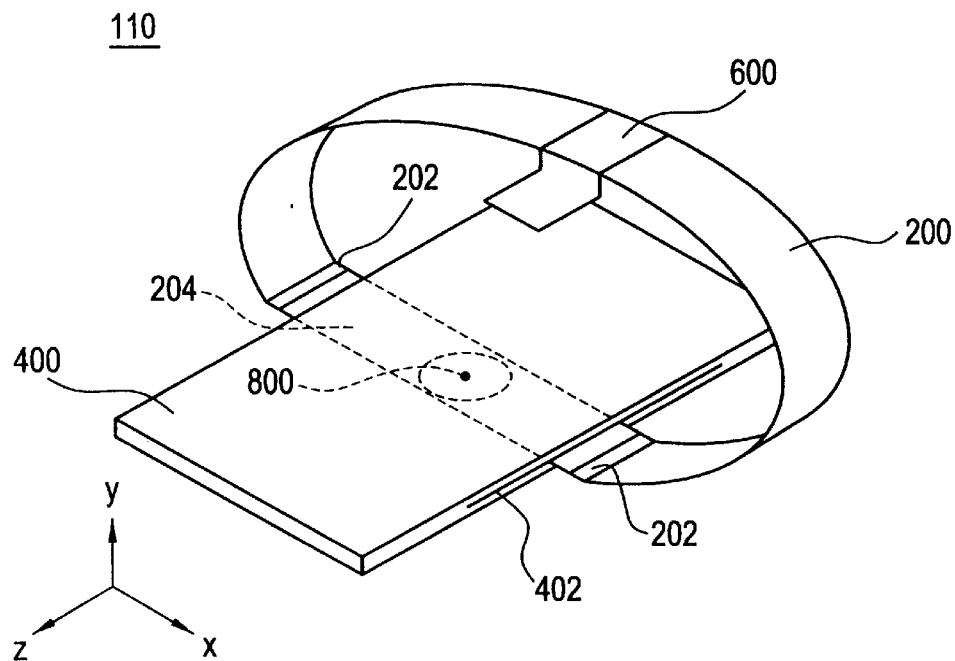
FIG. 2 is a schematic view illustrating the configuration of a receive coil section in the apparatus shown in FIG. 1.

FIG. 2 schematically shows the configuration of the receive coil section 110, which represents an embodiment of the RF coil of the present invention. In FIG. 2, x, y and z represent three directions orthogonal to one another. The x-direction is defined as the right-left direction, the y-direction as the upper-lower direction, and the z-direction as the coil axis direction, of the receive coil section 110. The same applies to other drawings which will be described later.

As shown, the receive coil section 110 has a coil body 200 and a coil base cover 400. The coil body 200 is attached with a puncture needle support tool 600. The coil body 200 is an embodiment of the coil body of the present invention. The coil body 200 is a solenoid coil. The puncture needle support tool 600 is an embodiment of the puncture needle support tool of the present invention, which will be described in more detail later.

The coil body 200 is comprised of two portions coupled by connectors 202. One of the two portions, which is shown as an upper portion in the drawing, is referred to as an upper structure, and the other, shown as a lower portion, is referred to as a lower structure hereinbelow. The lower structure constitutes a coil base 204.

The coil base cover 400 has therein a hollow portion, and apertures 402 opening to the hollow portion are formed on opposite lateral sides. The coil body 200 is rotatably supported at the central portion of the coil base 204 by a coil base supporting section 800 within the coil base cover 400. A portion consisting of the coil base supporting section 800 and coil base cover 400 is an embodiment of the supporting means of the present invention.

This supporting mechanism is used to appropriately adjust the rotation angle of the coil body 200 so that a desired site can be properly imaged. Since the puncture needle support tool 600 is attached to the coil body 200, the basic position of the puncture needle support tool 600 can be concomitantly adjusted without effort. In other words, coordination of positioning of the receive coil section 110 and positioning of the puncture needle support tool 600 can be improved.

Figure 3:
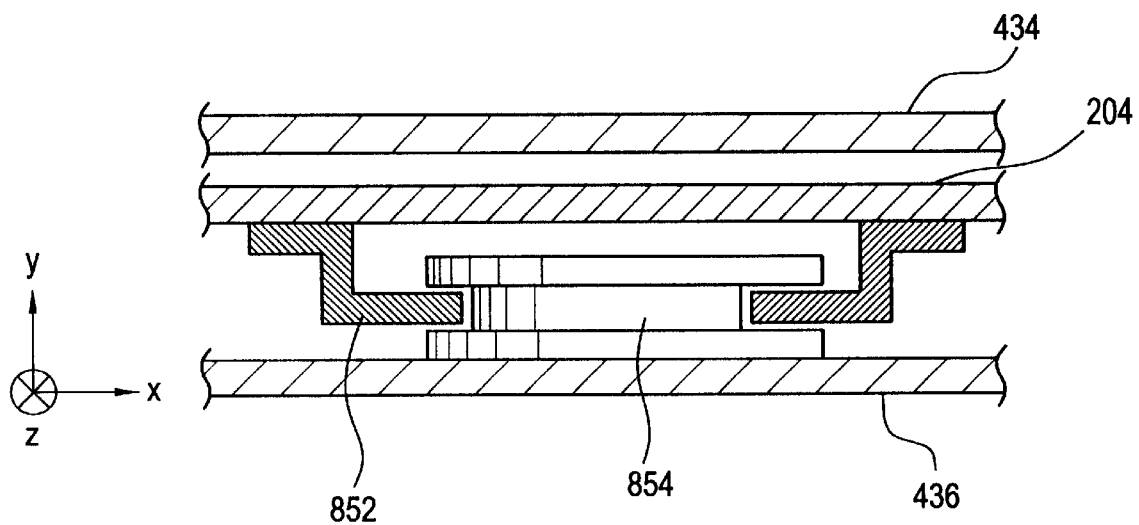
FIG. 3 is a schematic view illustrating the configuration of a coil base supporting section in the receive coil section shown in FIG. 2.

FIG. 3 schematically shows the configuration of the coil base supporting section 800 in cross section. As shown, a top plate 434 and a bottom plate 436 of the coil base cover 400 face each other in the y-direction across a vacant space. The coil base 204 is inserted into the vacant space. The coil base 204 is comprised of an inflexible plate material and an electric circuit formed thereon. The electric circuit constitutes part of a solenoid coil.

The lower surface of the coil base 204 is attached with a hub 852. The upper surface of the bottom plate 436 is attached with a pivot 854, which is engaged with the hub 852. The hub 852 and pivot 854 constitute the coil base supporting section 800. Such configuration of the coil base supporting section 800 allows the coil base 204 to rotate in the x-z plane in the drawing around the pivot 854.

The upper structure of the coil body 200 can be unfolded into a sheet-like shape as shown in FIG. 4. The unfolded upper structure of the coil body 200 is shown in detail in the partially broken-away view of FIG. 5. It should be noted that in FIG. 5 the proportion in the vertical direction is exaggerated for convenience of illustration.

As shown, the coil body 200 comprises a flexible substrate 360. The flexible substrate 360 is provided with an electric path pattern, which may be formed as a printed circuit, for example. The electric path constitutes part of a solenoid coil. On the longitudinal peripheries of the upper (in the drawing) surface of the flexible substrate 360 are disposed a pair of shape defining members 362 over the length of the flexible substrate 360. The upper surface of the flexible substrate 360 corresponds to the inner side when the cylindrical coil body is formed. The shape defining member 362 is made of plastic, for example.

The shape defining member 362 has a thickness in the y-direction such that flexibility is substantially avoided. The shape defining member 362 has a plurality of U-shaped notches 364. The notches 364 are cut in the z-direction and open upwards. The notches 364 have a depth approximately equal to the thickness of the shape defining member 362. Thus, the thickness at the bottom of the notch 364 is extremely reduced to obtain sufficient flexibility. Alternatively, the thickness at the bottom may be zero.

Figure 6:
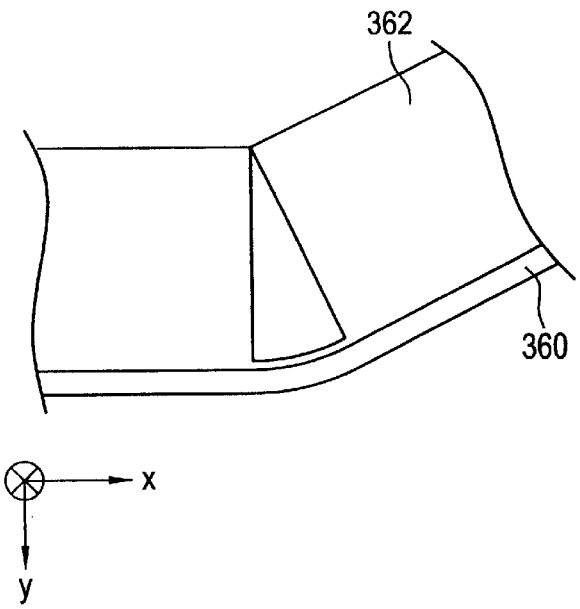
FIGS. 6 and 7 are schematic views illustrating part of the internal structure of the coil body of the receive coil section shown in FIG. 2.

Such a shape defining member 362 allows the flexible substrate 360 to bend only at the flexible portion of the shape defining member 362 (i.e., at the bottom of the notches) when the flexible substrate 360 is curved in the direction of forming a cylinder, and the bending amount is limited to that at which the openings of the notches 364 close, as schematically shown in FIG. 6. The allowable bending amount is determined by the width of the notches, i.e., the wider the width of the notches, the larger is the bending allowance range.

Figure 7:
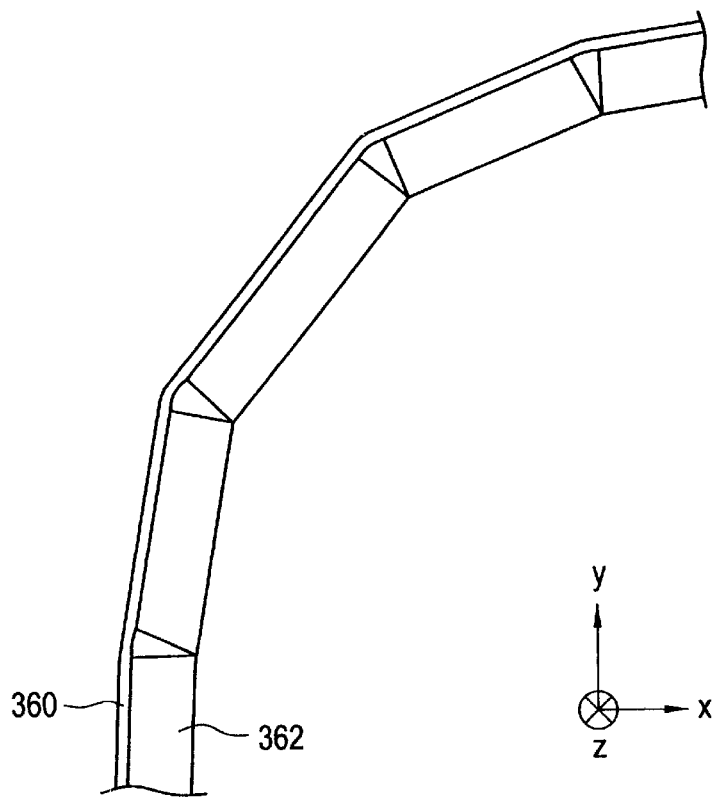

The width and the spacing of the notches 364 in the x-direction are determined according to the bending amount of every portion of the flexible substrate 360 in forming the cylinder. Thus, the bending of the flexible substrate 360, as exemplarily and schematically shown in FIG. 7, is given when the cylinder is formed. Such bending uniquely defines a curved shape of the coil body 200. By uniquely defining the curved shape, the electromagnetic condition of the coil body 200 is fixed, thereby enabling stable imaging.

Over the shape defining member 362 and the flexible substrate 360 is provided a shock absorbing member 366 of sponge, for example. A similar shock absorbing member 366 is also provided on the lower surface of the flexible substrate 360. All the above structures are enclosed in an envelope 368, which is secured to the connectors 202 at both ends of the coil body 200.

In the thus-configured receive coil section 110, the coil base cover 400 is placed on the cradle 500, and the object to be imaged 300 is rested over the coil base cover 400 thus placed. The coil base cover 400 has enough strength to bear the weight of the object to be imaged 300 without deformation.

Figure 8:
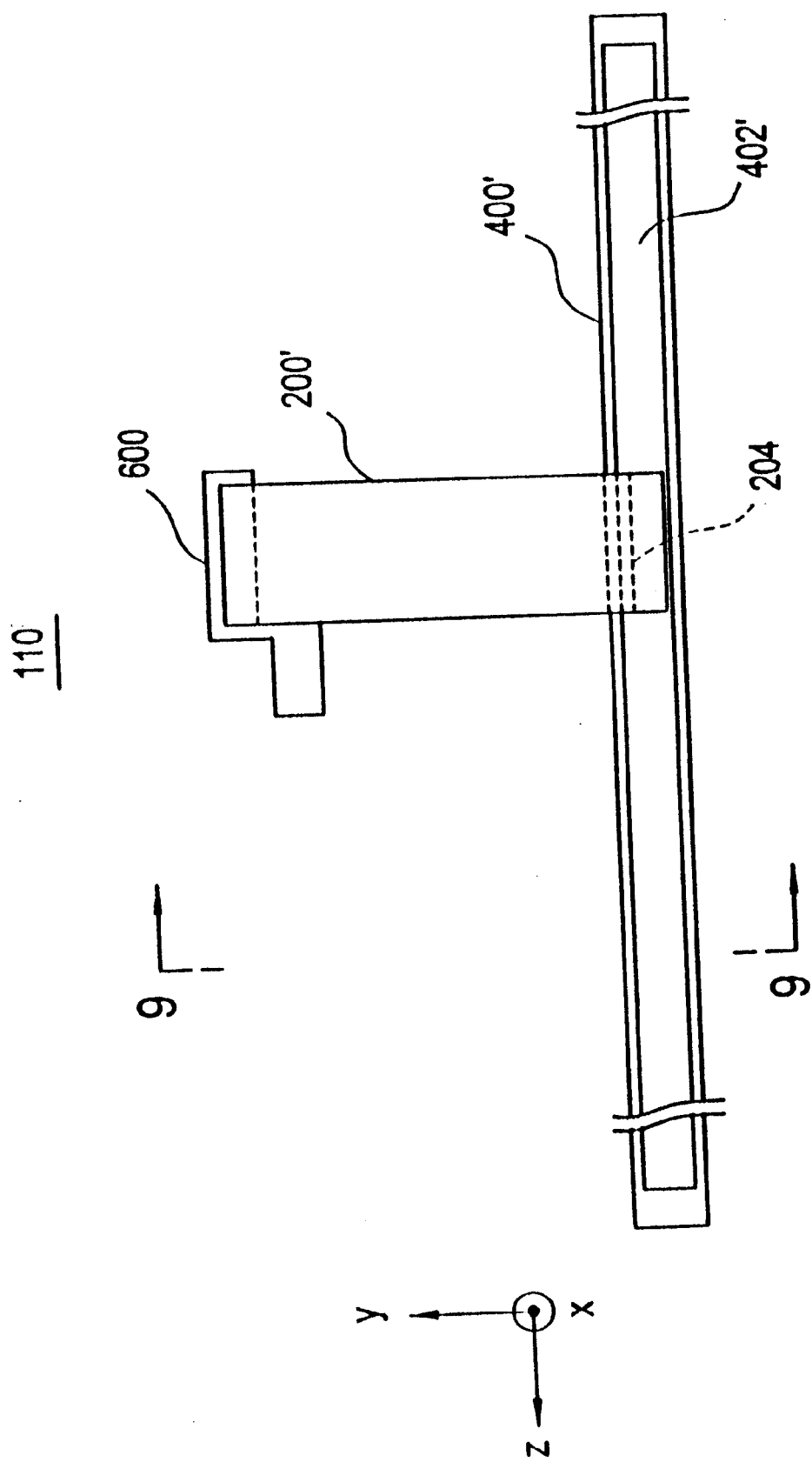
FIGS. 8 and 9 are schematic views illustrating another configuration of the receive coil section in the apparatus shown in FIG. 1.
Figure 9:
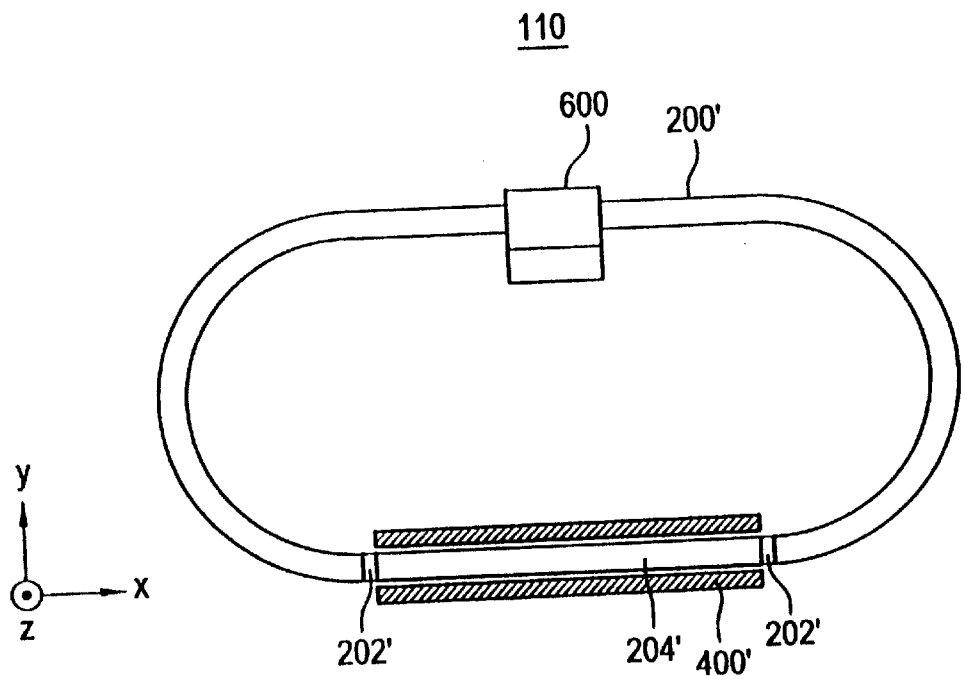

FIGS. 8 and 9 schematically show the configuration of another example of the receive coil section 110 as viewed from two directions perpendicular to each other. The configuration of the receive coil section 110 represents an embodiment of the RF coil of the present invention. FIG. 8 is a side view and FIG. 9 is a cross sectional view taken along line A—A, wherein x, y and z represent three directions orthogonal to one another. The x-direction is defined as the right-left direction, the y-direction as the upper-lower direction, and the z-direction as the coil axis direction, of the receive coil section 110. The same applies to other drawings which will be described later.

As shown in FIGS. 8 and 9, the receive coil section 110 has a coil body 200' and a coil base cover 400'. The coil body 200' is attached with a puncture needle support tool 600. The coil body 200' is an embodiment of the coil body of the present invention. The coil body 200' is a solenoid coil.

The coil body 200' is comprised of two portions coupled by connectors 202'. One of the two portions, which is shown as an upper portion in the drawing, is referred to as an upper structure, and the other, shown as a lower portion, is referred to as a lower structure hereinbelow. The lower structure constitutes a coil base 204'.

The upper structure of the coil body 200' is coupled to the coil base 204' via the connectors 202', forming a generally cylindrical shape as a whole. The upper structure of the coil body 200' has a similar configuration to that of the upper structure of the coil body 200 shown in FIG. 2.

The coil base cover 400' has therein a hollow portion, and apertures 402' opening to the hollow portion are formed on the opposite lateral sides. The coil base 204' is supported within the coil base cover 400' slidably in the z-direction. A portion consisting of the coil base 204' and coil base cover 400' is an embodiment of the supporting means of the present invention.

This mechanism is used to appropriately adjust the position of the coil body 200' in the body axis direction so that a desired site can be properly imaged. Since the puncture needle support tool 600 is attached to the coil body 200', the basic position of the puncture needle support tool 600 can be concomitantly adjusted without effort. In other words, coordination of positioning of the receive coil section 110 and positioning of the puncture needle support tool 600 can be improved.

Figure 10:
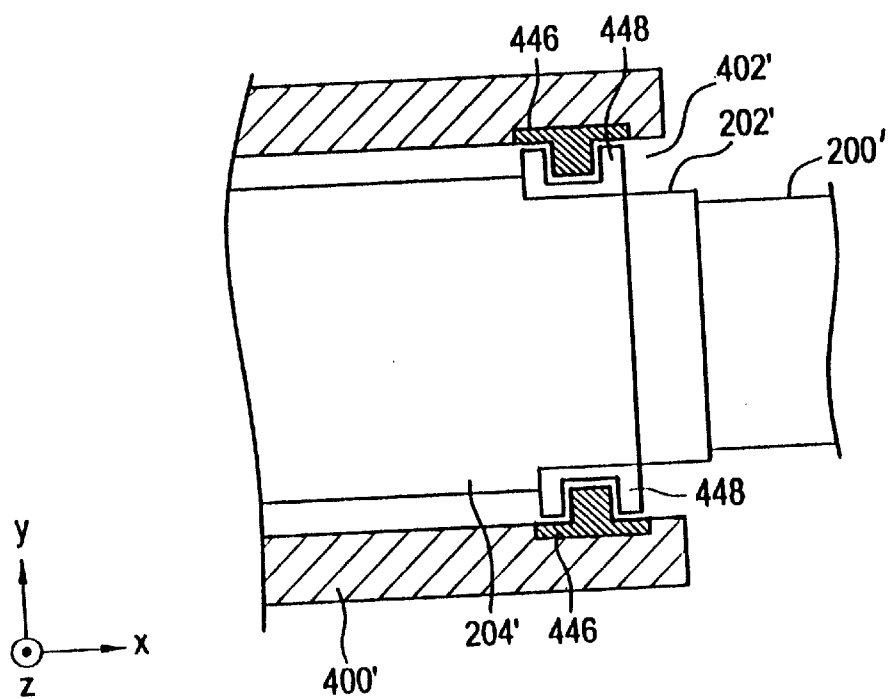
FIG. 10 is a schematic view illustrating the configuration of a coil base supporting section in the receive coil section shown in FIG. 8.

FIG. 10 shows an exemplary engagement structure between the coil base 204' and the coil base cover 400'. FIG. 10 is an enlarged view near the right end portion of the coil base cover 400' in FIG. 9. Although omitted from the drawing, the left end portion is configured symmetrically to the right end portion. As shown, the coil base cover 400' is provided with a pair of rails 446 disposed symmetrically with respect to the y-direction and over the length of the aperture 402' in the z-direction. The coil base 204' is provided with a pair of sliders 448 in engagement with the rails 446, thereby allowing the coil base 204' to slide in the z-direction within the aperture 402'.

In the thus-configured receive coil section 110', the coil base cover 400' is placed on the cradle 500, and the object to be imaged 300 is rested over the coil base cover 400' thus placed. The coil base cover 400' has enough strength to bear the weight of the object to be imaged 300 without deformation.

Figure 11:
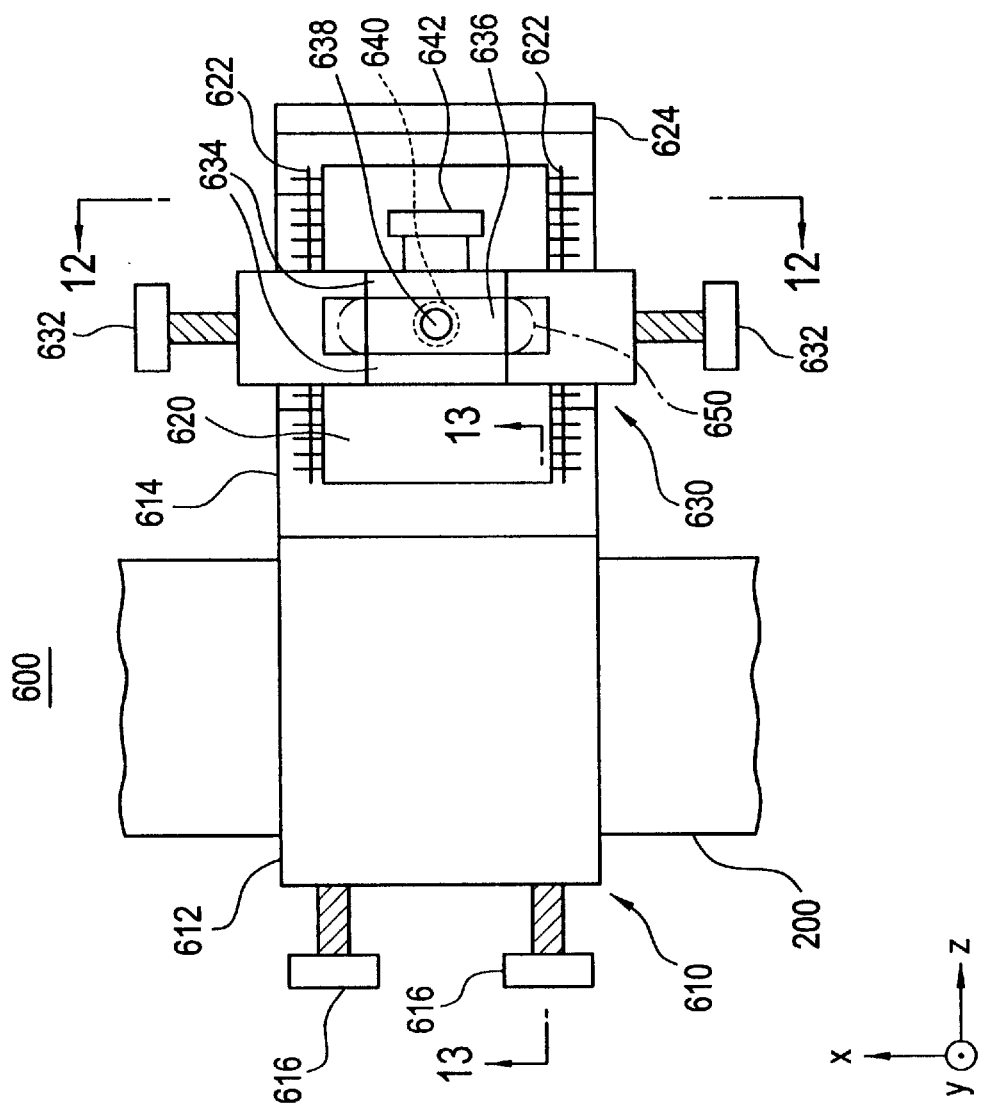
FIGS. 11–13 are schematic views illustrating the configuration of a puncture needle support tool.
Figure 12:
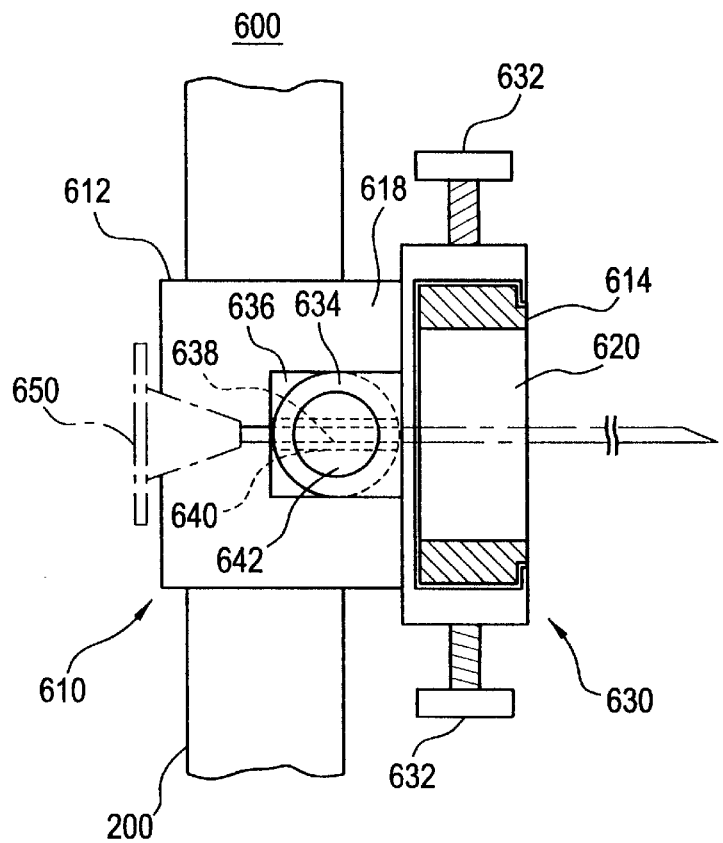
Figure 13:
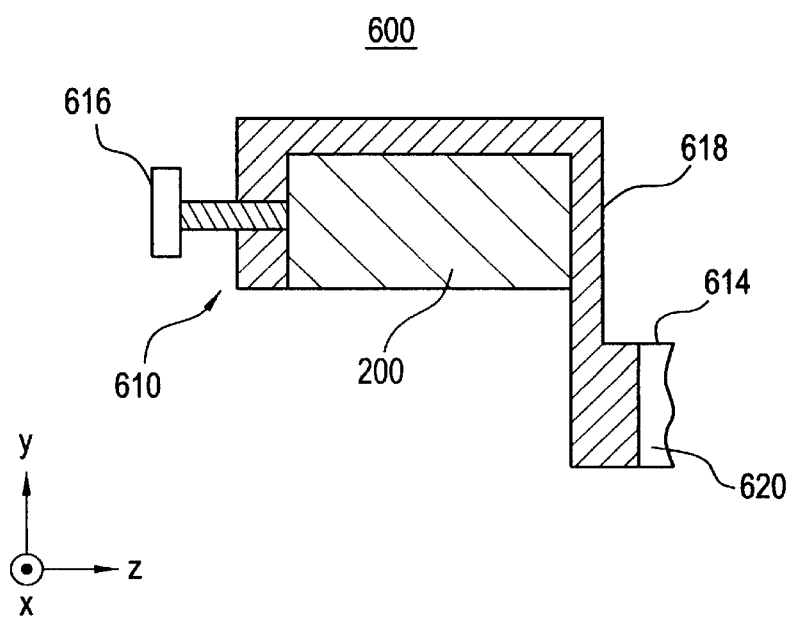

FIGS. 11, 12 and 13 schematically show the configuration of the puncture needle support tool 600. The configuration of the puncture needle support tool 600 represents an embodiment of the puncture needle support tool of the present invention. FIG. 11 is a plan view, FIG. 12 is a cross-sectional view taken along line B—B, and FIG. 13 is a cross-sectional view taken along. line C—C. As shown, the puncture needle support tool 600 has a base member 610, which is an embodiment of the first base member of the present invention. The base member 610 is made of a non-magnetic material. The same applies to components which will be described hereinafter.

The base member 610 has a coil straddling section 612 and a slide rail section 614. A slider 630 is slidably mounted on the slide rail section 614. The slider 630 is an embodiment of the second base member of the present invention.

The coil straddling section 612 has an inner peripheral structure conformed with the cross-sectional profile of the coil body 200 and can be mounted across the coil body 200. The coil straddling section 612 is an embodiment of the means for attachment to an RF coil of the present invention. The base member 610 is movable along the cylindrical outer peripheral surface of the coil body 200 while maintaining its straddling position. Moreover, the base member 610 can be secured to the coil body 200 by fastening knobs 616 having threaded shanks.

With the base member 610 thus straddling the coil base 200, the slide rail section 614 extends in the z-direction. In this condition, a tie section 618 between the slide rail section 614 and the coil straddling section 612 is sunk toward the axis of the coil body 200. The slide rail section 614 has an opening 620 between two parallel rails along the axial direction of the coil body 200. The slide rail section 614 also has a scale 622 indicative of the z-distance. One end of the slide rail section 614 is provided with a stopper 624 for preventing the slider 630 from dropping off.

The slider 630 straddles over the slide rail section 614 and is movable in the z-direction over the slide rail section 614. The slider 630 can be secured to the slide rail section 614 by fastening knobs 632 having threaded shanks.

The slider 630 has puncture needle guide supporting arms 634, which are a pair of arms provided on the slider 630 extending in a direction opposite to the opening 620. The arms face each other and hold a puncture needle guide 636 therebetween. The puncture needle guide 636 is an embodiment of the guide member of the present invention.

The puncture needle guide 636 has a through hole 638 toward the opening 620. The through hole 638 is an embodiment of the puncture needle passage of the present invention. A puncture needle 650 is inserted into the through hole 638 from the opposite side of the opening 620.

Near the through hole 638 and along the length of the through hole 638 is disposed an MR (magnetic resonance) marker 640, which is an embodiment of the MR marker of the present invention. A material having the same spin behavior as that of hydrogen atoms in the object to be imaged 300, such as nickel chloride solution, is employed as the MR marker 640. Such a material is encapsulated in an appropriate container disposed along the length of the through hole 638 and employed as the MR marker.

The puncture needle guide 636 has shafts, which will be described later, extending in a direction perpendicular to the through hole 638, and is rotatable around the shafts. One of the shafts protrudes outwards in the z-direction through one arm of the pair of supporting arms. A thread is provided on the protruding portion, and a knob 642 is attached to the thread. The puncture needle guide 636 can be secured to the puncture needle guide supporting arms 634 by fastening the knob 642, and the puncture needle guide 636 can be made rotatable by loosening the knob 642.

Figure 14:
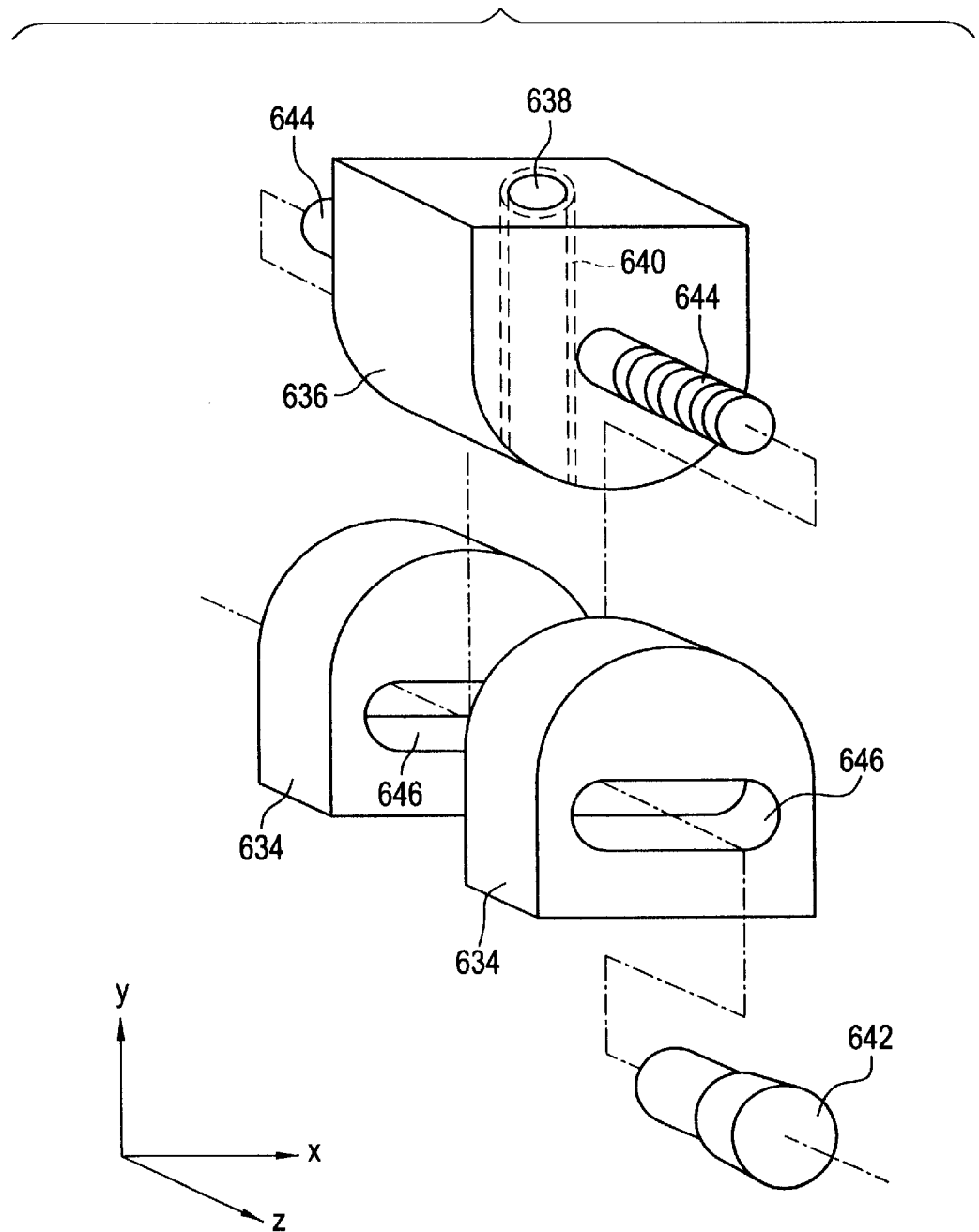
FIG. 14 is a schematic view illustrating the configuration of part of the puncture needle support tool.

The configuration of a portion consisting of the puncture needle guide supporting arms 634, puncture needle guide 636 and knob 642 will now be described in more detail with reference to FIG. 14. As shown, the puncture needle guide 636 has a pair of shafts 644 on its opposite lateral sides. The shafts 644 are perpendicular to the length of the through hole 638.

Each puncture needle guide supporting arm 634 is provided with a horizontally elongated hole 646 corresponding to each shaft 644, and the puncture needle guide 636 is supported by the puncture needle guide supporting arms 634 via the holes 646 as bearings for the shafts 644. The shafts 644 are rotatable within the holes 646 and are movable in the major axis direction of the hole 646. One shaft of the pair of shafts 644 has a threaded portion, and a nut provided on the knob 642 engages with the threaded portion.

Using the puncture needle support tool of such configuration, the basic puncture position can be adjusted around the body axis of the object to be imaged 300 by changing the position where the base member 610 is attached to the coil body 200.

Moreover, the puncture position can be adjusted in the object's body axis direction by changing the position of the slider 630 on the base member 610. Furthermore, the puncture position and angle can be finely adjusted by adjusting the transverse moving distance and rotational angle of the puncture needle guide 636 on the slider 630.

When such kinds of adjustment are being attempted during magnetic resonance imaging, an image of the MR marker 640 disposed in the puncture needle guide 636 is displayed on the screen. Since the MR marker 640 is disposed along the through hole 638 for passing the puncture needle 650, the image is indicative of the position and direction of puncture by the puncture needle 650.

Thus, the operator can easily determine a proper puncture direction because he/she can recognize the positional relationship between a region of interest and the MR marker 640 from their images displayed on the screen.

When the puncture direction has been determined, all the knobs are fastened to secure all the movable portions. Specifically, when a basic puncture position has been determined, the knobs 616 are fastened to secure the puncture needle support tool 600 to the coil body 200. When a puncture position in the objects body axis direction has been determined, the knobs 632 are fastened to secure the slider 630 to the base member 610. After fine adjustment of the puncture position and angle, the knob 642 is fastened to secure the puncture needle guide 636 to the slider 630.

Then, the puncture needle 650 is inserted into the through hole 638 in the puncture needle guide 636, and puncture is performed. The puncture is also performed concurrently with imaging. If a puncture needle comprising an MR marker is employed as the puncture needle 650, the puncture needle 650 can be imaged within the object to be imaged 300.

The operation of the present apparatus will now be described. The receive coil section 110 is mounted at a predefined position on the cradle 500; the upper structure of the coil body 200 is next removed to rest the object to be imaged 300; and then the upper structure of the coil body 200 is attached via the connectors 202. The relative positional relationship between the coil body 200 and the object to be imaged 300 at this time is exemplarily shown in FIG. 15.

Figure 15:
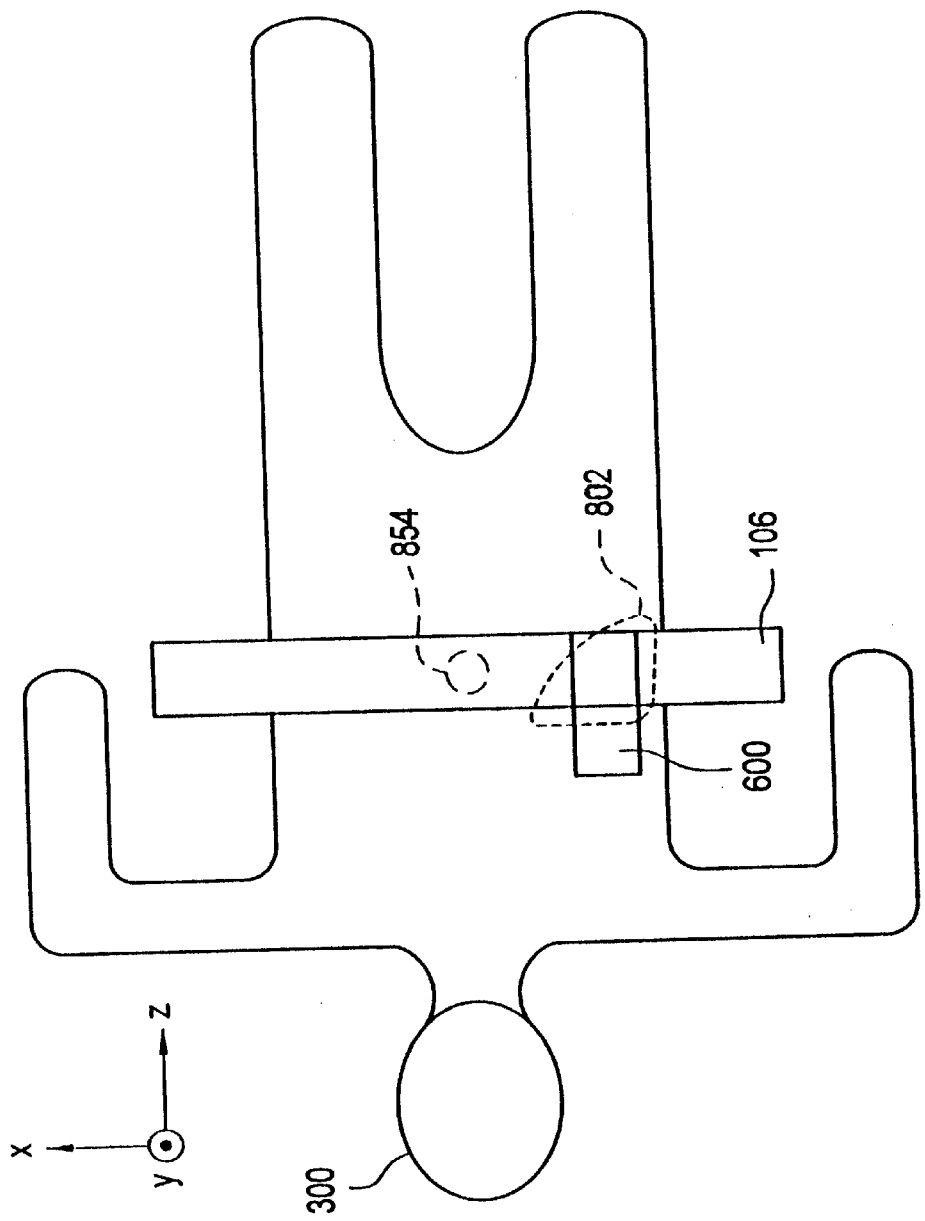
FIG. 15 is a schematic view illustrating the relative positional relationship between an object to be imaged and the coil body.

FIG. 15 shows the positional relationship between the coil body 200 and the object to be imaged 300 in imaging the liver, and shows that the coil body 200 surrounds a site of the liver 802 in the trunk of the object to be imaged 300. The object to be imaged 300 is carried into the internal space of the static magnetic field generating section 2 in this state and imaging is started.

The imaging proceeds under control of the control section 160. FIGS. 16(A)–16(E) show an exemplary pulse sequence for use in magnetic resonance imaging. The illustrated pulse sequence is one in accordance with a spin echo (SE) technique.

Figures 16A, 16B, 16C, 16D, 16E:
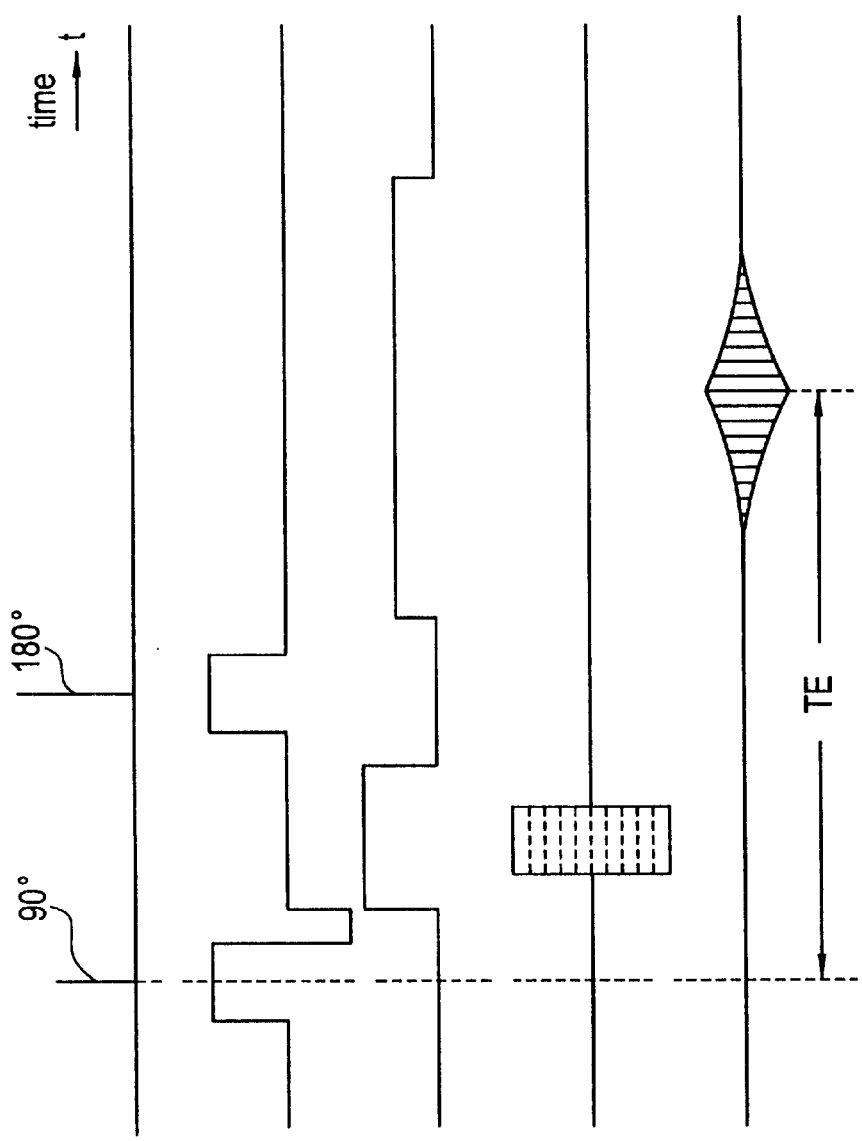

Specifically, FIG. 16(A) is a sequence of 90° and 180° pulses for RF excitation of the SE technique, and FIGS. 16(B)–16(E) are sequences of a slice gradient Gs, a readout gradient Gr, a phase encoding gradient Gp and a spin echo MR, respectively, of the SE technique. It should be noted that the 90° and 180° pulses are represented by their respective central signals. The pulse sequence proceeds from the left to the right along a time axis t.

As shown, the 90° pulse achieves 90° excitation of the spins. At the same time, the slice gradient Gs is applied to achieve selective excitation for a certain slice. After a predetermined time from the 90° excitation, 180° excitation by the 180° pulse, or spin inversion, is performed. Again, the slice gradient Gs is applied at the same time to achieve selective inversion for the same slice.

During the period between the 90° excitation and spin inversion, the readout gradient Gr and phase encoding gradient Gp are applied. The readout gradient Gr dephases the spins, and the phase encoding gradient Gp phase-encodes the spins.

After the spin inversion, the spins are rephased by the readout gradient Gr to generate a spin echo MR. The spin echo MR is an RF signal having a symmetric waveform with respect to the echo center. The central echo occurs after TE (echo time) from the 90° excitation. The spin echo MR is collected by the data acquisition section 150 as view data. Such a pulse sequence is repeated 64–512 times in a cycle of TR (repetition time). The phase encoding gradient Gp is varied for each repetition to provide a different phase encoding each time. Thus, view data for 64–512 views are obtained.

Another example of the pulse sequence for magnetic resonance imaging is shown in FIGS. 17(A)–17(E). This pulse sequence is one in accordance with a gradient echo (GRE) technique.

Specifically, FIG. 17(A) a sequence of an α° pulse for RF excitation of the GRE technique, and FIGS. 17(B)–17(E) are sequences of a slice gradient Gs, a readout gradient Gr, a phase encoding gradient Gp and a gradient echo MR, respectively, of the GRE technique. It should be noted that the α° pulse is represented by its central signal. The pulse sequence proceeds from the left to the right along a time axis t.

As shown, the α° pulse achieves α° excitation of the spins, wherein a is not greater than 90. At the same time, the slice gradient Gs is applied to achieve selective excitation for a certain slice.

After the α° excitation, the spins are phase-encoded by the phase encoding gradient Gp. Next, the spins are first dephased and are subsequently rephased by the readout gradient Gr to generate a gradient echo MR. The gradient echo MR is an RF signal having a symmetric waveform with respect to the echo center. The central echo occurs after TE from the α° excitation.

The gradient echo MR is collected by the data acquisition section 150 as view data. Such a pulse sequence is repeated 64–512 times in a cycle of TR. The phase encoding gradient Gp is varied for each repetition to provide a different phase encoding each time. Thus, view data for 64–512 views are obtained.

The view data obtained by the pulse sequence of FIGS. 16(A)–16(E) or FIGS. 17(A)–17(E) are collected into the memory in the data processing section 170. It will be easily recognized that the pulse sequence is not limited to that of the SE or GRE technique, but may be that of any other appropriate technique such as a fast spin echo (FSE) technique.

The data processing section 170 performs a two-dimensional inverse Fourier transformation on the view data to reconstruct a tomographic image of the object to be imaged 300. The reconstructed image is displayed by the display section 180 as a visible image. Thus, a tomographic image of the liver 802 is displayed. A medical operation, such as biopsy, on the liver 802 is performed with reference to the tomographic image. The biopsy is performed concurrently with the imaging described above, that is, interventional imaging is performed.

Figure 18:
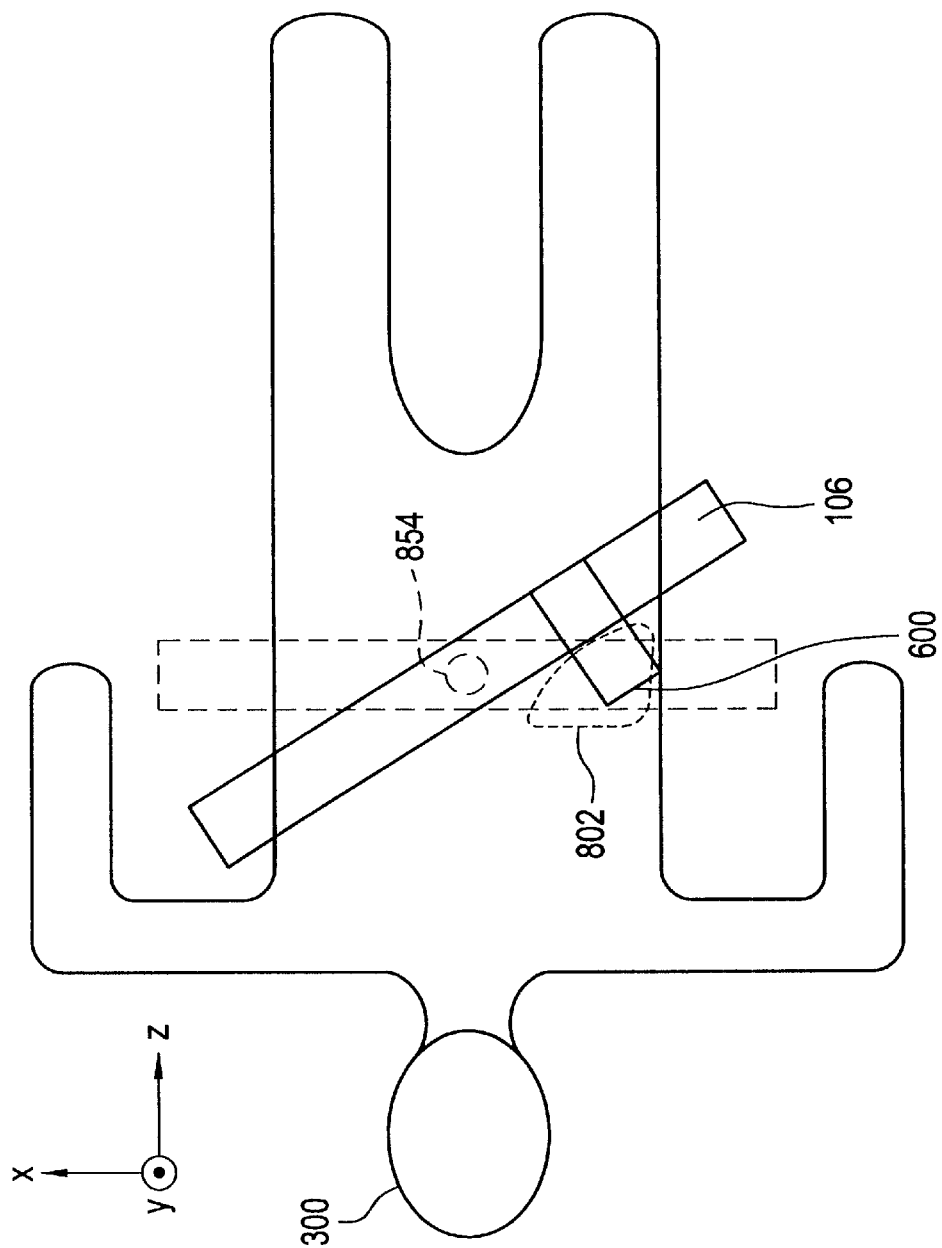
FIG. 18 is a schematic view illustrating the relative positional relationship between the object to be imaged and the coil body.

In the interventional imaging, the coil body 200 is rotated around the axis 854, resulting in a positional relationship oblique to the object to be imaged 300. Thus, the relative obliquity of the coil body 200 with respect to the object to be imaged 300 is changed, whereby the positional relationship between the object to be imaged 300 and the coil body 200 becomes as exemplarily shown in FIG. 18. Specifically, the coil body 200 is shifted in the right direction in the drawing from the original position indicated by broken line, and is made not to overlap the liver 802.

It should be noted that when a receive coil section having the coil body 200 movable in the object's body axis direction, as shown in FIG. 8, is employed as the receive coil section 110, the coil body 200 is made not to overlap the liver 802 by translating the coil body 200 in the object's body axis direction.

Thus, access to the liver for biopsy is facilitated because it is hampered by the coil body 200. Since the sensitivity range of the coil body 200 encompasses the liver 802 even in this position, it is possible to obtain a tomographic image of the liver 802 with a sufficient SNR (signal-to-noise ratio) based on received magnetic resonance signals. Therefore, interventional imaging can be effectively carried out. Then, the operator performs puncture on the liver 802 after adjustment of the basic position of the puncture needle support tool 600, adjustment of the puncture position in the objects body axis direction, and fine adjustment of the puncture direction, as described before.

While the preceding description is made in the context of puncturing the liver, those skilled in the art can easily recognize that interventional imaging is not limited to being performed on the liver, but may be performed on other tissues. Moreover, the coil body is not limited to being employed for reception but may be employed for transmission of the RF signals.

Many widely different embodiments of the invention may be configured without departing from the spirit and the scope of the present invention. It should be understood that the present invention is not limited to the specific embodiments described in the specification, except as defined in the appended claims.

What is claimed is:

1. An RF coil comprising:
   a coil body forming a loop adapted to surround an object to be imaged; and
   a puncture needle support tool engaged with said coil body; wherein said puncture needle support tool comprises:
      a first base member having means for attachment to the RF coil;
      a second base member attached to said first base member movably in a direction substantially parallel to the axis of said RF coil; and
      a guide member comprising a puncture needle passage, and attached to said second base member movably in a direction substantially perpendicular to the axis of said RF coil and rotatably in a plane substantially perpendicular to the axis of said RF coil.

2. The RF coil as defined in claim 1, further comprising supporting means for supporting said coil body so that a position of said coil body relative to said object to be imaged can be changed.

3. A magnetic resonance signal measuring apparatus comprising:
   an RF coil comprising: a coil body forming a loop adapted to surround an object to be imaged, and a puncture needle support tool engaged with said coil body; and
   magnetic resonance signal measuring means connected to a body of said RF coil;
   wherein said puncture needle support tool comprises:
      a first member having means for attachment to said RF coil;
      a second base member attached to said first base member movably in a direction substantially parallel to the axis of said RF coil; and
      a guide member comprising:
         a puncture needle passage and an MR marker disposed along said puncture needle passage, and attached to said second base member movably in a direction substantially perpendicular to the axis of said RF coil and rotatably in a plane substantially perpendicular to said axis of said RF coil.

4. The apparatus of claim 3, further comprising supporting means for supporting said coil body so that a position of said coil body relative to said object to be imaged can be changed.

5. A magnetic resonance imaging apparatus comprising:
   static magnetic field generating means for generating a static magnetic field in a space containing an object to be imaged;
   gradient magnetic field generating means for generating a gradient magnetic field in said space;
   high frequency magnetic field generating means for generating a high frequency magnetic field in said space;
   measuring means for measuring a magnetic resonance signal from said space; and
   image producing means for producing an image based on said measured magnetic resonance signal; wherein
      said measuring means comprises a magnetic resonance signal measuring means connected to a body of an RF coil, said RF coil comprising:
         a coil body forming a loop adjusted to surround said object to be imaged, and a puncture needle support tool engaged with said coil body; wherein said puncture needle support tool comprises:
            a first base member having means for attachment to said RF coil;
            a second base member attached to said first base member movably in a direction substantially parallel to the axis of said RF coil; and
            a guide member comprising a puncture needle passage and an MR marker disposed along said puncture needle passage, and attached to said second base member movably in a direction substantially perpendicular to the axis of said RF coil and rotatably in a plane substantially perpendicular to the axis of said RF coil.

6. The apparatus of claim 5, further comprising supporting means for supporting said coil body so that a position of said coil body relative to said object to be imaged can be changed.

7. A magnetic resonance imaging method comprising the steps of:
   generating a static magnetic field in a space containing an object to be imaged;
   generating a gradient magnetic field in said space;
   generating a high frequency magnetic field in said space;
   measuring a magnetic resonance signal from said space; and
   producing an image based on said measured magnetic resonance signal; wherein said measuring step is carried out by a magnetic resonance signal measuring apparatus comprising:
      an RF coil and
      magnetic resonance signal measuring means connected to a body of said RF coil comprising:
         a coil body forming a loop adapted to surround an object to be imaged; and
         a puncture needle support tool engaged with said coil body; wherein said puncture needle support tool comprises:
            a first base member having means for attachment to the RF coil;
            a second base member attached to said first base member movably in a direction substantially parallel to the axis of said RF coil; and
            a guide member comprising a puncture tool passage and an MR marker disposed along said puncture needle passage, and attached to said second base member movably in a direction substantially perpendicular to the axis of said RF oil and rotatably in a plane substantially perpendicular to the axis of said RF coil.

8. The method of claim 7, wherein said RF coil further comprises supporting means for supporting said coil body so that a position of said coil body relative to said object to be imaged can be changed.

* * * * *